(12) United States Patent
Mayama

(10) Patent No.: US 8,338,391 B2
(45) Date of Patent: Dec. 25, 2012

(54) PHOSPHINE-BORANE COMPOUND AND METHOD FOR PRODUCING THE SAME, AND METHOD FOR PRODUCING HYDROGEN-PHOSPHINE-BORANE COMPOUND

(75) Inventor: Daisuke Mayama, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 571 days.

(21) Appl. No.: 12/637,999

(22) Filed: Dec. 15, 2009

(65) Prior Publication Data

US 2010/0152489 A1 Jun. 17, 2010

(30) Foreign Application Priority Data

Dec. 15, 2008 (JP) ................. 2008-317786

(51) Int. Cl.
*A61K 31/69* (2006.01)
*C07F 5/02* (2006.01)
(52) U.S. Cl. ............................. 514/64; 564/8
(58) Field of Classification Search .............. 514/64; 564/8
See application file for complete search history.

(56) References Cited

U.S. PATENT DOCUMENTS
2007/0021610 A1   1/2007   Imamoto et al.

FOREIGN PATENT DOCUMENTS
| EP | 0997470 A1 | 5/2000 |
| EP | 0997471 A1 * | 5/2000 |
| JP | 2972887 B1 | 3/1999 |
| JP | 2007-56007 A | 3/2007 |

OTHER PUBLICATIONS

Nobihiko Oohara et al., "Reaction of t-Butylphosphine-Borane with Various Electrophiles and Synthesis of Optically Active t-Butylmethylphospine-Borane"; The Chemical Society of Japan, 2002, pp. 1359-1365, vol. 75.

Takeshi Ohkuma, et al.; "Asymmetric Hydrogenation", Catalytic Asymmetric Synthesis, Second Edition, pp. 1-7, 2000.
Ryoji Noyori; "Asymmetric Catalysis In Organic Synthesis". A Wiley-Interscience Publication, 1994, pp. 1-15.

\* cited by examiner

*Primary Examiner* — Kamal Saeed
*Assistant Examiner* — Janet L Coppins
(74) *Attorney, Agent, or Firm* — Westerman, Hattori, Daniels & Adrian, LLP

(57) ABSTRACT

An object of the present invention is to provide an optically active phosphine-borane compound and a method for producing the same which are useful for the production of an optically active phosphine ligand and allow easy production of any antipode. There is provided a phosphine-borane compound represented by the following general formula (P-1). There is also provided a method for producing the phosphine-borane compound, the method comprising subjecting a hydrogen-phosphine-borane compound represented by the following general formula (P-2) to a coupling reaction with an optically active isocyanate compound represented by the following general formula (3). In the following formulae, $R^1$ and $R^2$ each represent a hydrogen atom, a hydrocarbon group, or a substituted hydrocarbon group and may be selected so that asymmetry may be induced on the phosphorus atom by the presence of these groups, or may be selected so that asymmetry may not be induced; and $R^3$ represents an asymmetric hydrocarbon group or an asymmetric substituted hydrocarbon group.

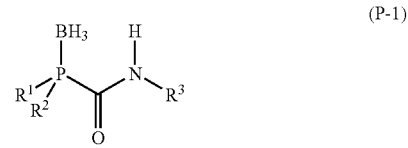

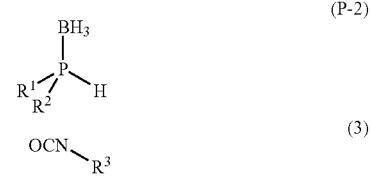

7 Claims, No Drawings

PHOSPHINE-BORANE COMPOUND AND METHOD FOR PRODUCING THE SAME, AND METHOD FOR PRODUCING HYDROGEN-PHOSPHINE-BORANE COMPOUND

BACKGROUND OF THE INVENTION

1. Field of the Invention

The present invention relates to a new phosphine-borane compound and a method for producing the same. The new phosphine-borane compound of the present invention is useful as a raw material of an optically active phosphine ligand precursor frequently used as a raw material of the catalyst for an asymmetric synthesis reaction. The present invention also relates to a method for producing a hydrogen-phosphine-borane compound useful as an optically active phosphine ligand precursor.

2. Description of the Related Art

An organic synthesis reaction using a metal complex having an optically active phosphine ligand as a catalyst have been known for many years, and many results of research have been reported because it is very useful. Many optically active phosphine compounds of various structures have been developed in order to increase catalyst performance as described, for example, in "Asymmetric Synthesis in Organic Synthesis", by Ryoji Noyori, John Willy & Sons, Inc., 1994, Canada (Review on optically active phosphine ligands) and "Catalytic Asymmetric Synthesis", edited by Iwao Ojima, Wiley-VCH, Inc., 2000, Canada (Review on optically active phosphine ligands).

In recent years, a ligand which makes the phosphorus atom itself asymmetric has been developed and is reported to provide an excellent effect (for example, refer to Japanese Patent No. 2972887). In this case, an optically active phosphine ligand precursor is often supplied as a phosphine-borane in which an easily oxidized part is protected by a borane because the precursor is highly oxidizable and unstable. Many raw materials have been developed as a raw material of the precursor. Among others, a hydrogen-phosphine-borane having a P—H bond is one of the useful compound groups as a raw material of this precursor because the P anion works as a nucleophilic group and easily forms a P—C bond.

As a method for producing a hydrogen-phosphine-borane compound, there is mentioned a first method in which an alkyl (or aryl) dimethylphosphine-borane is allowed to react with butyllithium in the presence of (−)-sparteine at an ultra low temperature (−78° C.) to yield an asymmetric lithium methylene alkyl (or aryl) methylphosphine-borane, which is then oxidized by oxygen to yield an optically active alkyl (or aryl) methyl(hydroxymethyl)phosphine-borane, which is then oxidatively eliminated with potassium persulfate in the presence of ruthenium chloride (III) to produce an optically active hydrogen-phosphine-borane (for example, refer to Japanese Patent Laid-Open No. 2007-56007). Further, there is mentioned a second method in which a racemic hydrogen-phosphine-borane is allowed to couple with a chloroformate of an asymmetric alcohol to form a diastereomer, which is optically resolved by crystallization and then decomposed to produce an optically active hydrogen-phosphine-borane (for example, refer to Bull. Chem. Soc. Jpn., 75(6), (2002), 1359-1365).

However, a reversed type of stereoisomer cannot be obtained since natural (−)-sparteine is used in the first method using (−)-sparteine. Further, a compound showing properties equivalent to the reversed type of sparteine has been obtained by chemical synthesis through various difficulties in recent years. However, the compound is not easily available at present, and it is not regarded as an industrially useful means for obtaining a reversed type of stereoisomer (for example, refer to J.A.C.S, 128 (2006), 9336-9337). In addition, in the first method, the reaction requires a low temperature of −78° C., which requires a huge investment for reaction facilities. On the other hand, the second method using a chloroformate of an asymmetric alcohol is also based on the asymmetry of a natural alcohol in many cases. Therefore, it is often difficult to obtain a reversed type of stereoisomer.

Therefore, a development of a method has been desired which has high generality and allows production of any antipode without a special apparatus such as an ultra-low temperature cooling device when producing an optically active phosphine-borane compound.

Therefore, an object of the present invention is to provide an optically active phosphine-borane compound and a method for producing the same which are useful for the production of an optically active phosphine ligand frequently used as a raw material of the catalyst for an asymmetric synthesis reaction and allow easy production of any antipode.

SUMMARY OF THE INVENTION

As a result of extensive studies, the present inventor has succeeded in synthesizing a diastereomer of a new phosphine-borane compound which is optically resolvable by subjecting a racemic hydrogen-phosphine-borane compound to a coupling reaction with an optically active isocyanate compound. The present inventor has also found that this phosphine-borane compound is decomposed to give an optically active hydrogen-phosphine-borane compound frequently used as a raw material of the catalyst for an asymmetric synthesis reaction, with a reduced number of steps at high efficiency. The present invention has been reached based on these findings.

Specifically, the present invention provides the following 1) to 5).

1) A phosphine-borane compound represented by general formula (P-1):

[Formula 1]

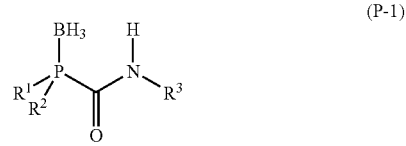

wherein $R^1$ and $R^2$ each independently represent a hydrogen atom, a hydrocarbon group, or a substituted hydrocarbon group; and $R^3$ represents an asymmetric hydrocarbon group or an asymmetric substituted hydrocarbon group.

2) The phosphine-borane compound as described above, wherein the phosphine-borane compound is represented by general formula (1):

[Formula 2]

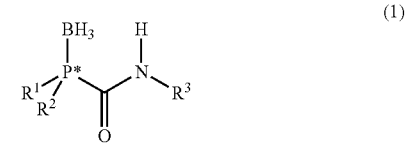

wherein $R^1$ and $R^2$ are a pair of groups which induce asymmetry on the phosphorus atom by the presence of these groups or form an asymmetry plane using the phosphorus atom as a point of the plane, wherein the $R^1$ and $R^2$ each represent a hydrogen atom, a hydrocarbon group, or a substituted hydrocarbon group; $R^3$ represents an asymmetric hydrocarbon group or an asymmetric substituted hydrocarbon group; and the asterisk * represents asymmetry.

3) A method for producing a phosphine-borane compound represented by the above general formula (P-1), the method comprising subjecting a hydrogen-phosphine-borane compound represented by general formula (P-2):

[Formula 3]

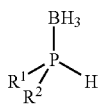

(P-2)

(wherein $R^1$ and $R^2$ have the same meaning as in the above general formula (P-1)) to a coupling reaction with an optically active isocyanate compound represented by general formula (3):

[Formula 4]

(3)

wherein $R^3$ has the same meaning as in the above general formula (P-1).

4) A method for producing a phosphine-borane compound represented by the above general formula (1), the method comprising the steps of subjecting a hydrogen-phosphine-borane compound represented by general formula (2):

[Formula 5]

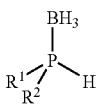

(2)

(wherein $R^1$ and $R^2$ have the same meaning as in the above general formula (1)) to a coupling reaction with an optically active isocyanate compound represented by general formula (3):

[Formula 6]

(3)

wherein $R^3$ has the same meaning as in the above general formula (1); and then purifying the resulting compound by optical resolution.

5) A method for producing an optically active hydrogen-phosphine-borane compound represented by general formula (4):

[Formula 7]

(4)

wherein $R^1$, $R^2$, and the asterisk * have the same meaning as in the above general formula (1), the method comprising subjecting a compound represented by the above general formula (1) to a decomposition reaction.

The present invention can provide a new optically active phosphine-borane compound and a method for producing the same which are useful for the production of an optically active phosphine ligand frequently used as a raw material of the catalyst for an asymmetric synthesis reaction and allow easy production of any antipode. The present invention can also provide a method for easily producing a hydrogen-phosphine-borane compound useful as an optically active phosphine ligand precursor by using the above phosphine-borane compound as a raw material.

DETAILED DESCRIPTION OF THE PREFERRED EMBODIMENTS

The phosphine-borane compound of the present invention is represented by the following general formula (P-1):

[Formula 8]

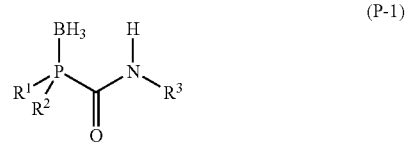

(P-1)

wherein $R^1$ and $R^2$ each independently represent a hydrogen atom, a hydrocarbon group, or a substituted hydrocarbon group; and $R^3$ represents an asymmetric hydrocarbon group or an asymmetric substituted hydrocarbon group.

In the above general formula (P-1), $R^1$ and $R^2$ may be selected so that the $R^1$ and $R^2$ serve as a pair of groups which induce asymmetry on the phosphorus atom by the presence of these groups or form an asymmetry plane using the phosphorus atom as a point of the plane, or may be selected so that such asymmetry may not be induced. When $R^1$ and $R^2$ are selected so that such asymmetry may be induced, the phosphine-borane compound of the present invention is represented by the following general formula (1):

[Formula 9]

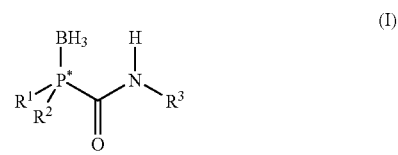

(I)

wherein $R^1$ and $R^2$ are a pair of groups which induce asymmetry on the phosphorus atom by the presence of these groups or form an asymmetry plane using the phosphorus atom as a point of the plane, wherein the $R^1$ and $R^2$ each represent a hydrogen atom, a hydrocarbon group, or a substituted hydrocarbon group; $R^3$ represents an asymmetric hydrocarbon group or an asymmetric substituted hydrocarbon group; and the asterisk * represents asymmetry.

The hydrogen-phosphine-borane compound used in the method for producing the phosphine-borane compound of the present invention is represented by the following general formula (P-2):

[Formula 10]

(P-2)

wherein $R^1$ and $R^2$ have the same meaning as in the above general formula (P-1).

When the phosphine-borane compound of the present invention is represented by the above general formula (1), the hydrogen-phosphine-borane compound used for producing the same is represented by the following general formula (2):

[Formula 11]

(2)

wherein $R^1$ and $R^2$ have the same meaning as in the above general formula (1). As the hydrogen-phosphine-borane compound represented by the above general formula (2), a racemic form can be used, for example.

The optically active isocyanate compound used for the production of the phosphine-borane compound of the present invention is represented by the following general formula (3):

[Formula 12]

(3)

wherein $R^3$ represents an asymmetric hydrocarbon group or an asymmetric substituted hydrocarbon group.

The optically active hydrogen-phosphine-borane compound obtained by decomposing the phosphine-borane compound of the present invention represented by the above general formula (1) is represented by the following general formula (4):

[Formula 13]

(4)

wherein $R^1$, $R^2$, and the asterisk * have the same meaning as in the above general formula (1).

The groups represented by $R^1$ and $R^2$ in the above general formulae (P-1), (1), (P-2), (2), and (4) will now be described.

$R^1$ and $R^2$ each represent a hydrogen atom, a hydrocarbon group, or a substituted hydrocarbon group. $R^1$ and $R^2$ may be independent of each other, or they may be connected by crosslinking.

Examples of the hydrocarbon group include, but are not limited to, an alkyl group, an aralkyl group, and an aryl group.

The alkyl group may be linear, branched, or cyclic. Examples of the linear or branched alkyl group include a linear or branched alkyl group having 1 to 8 carbon atoms, specifically including a methyl group, an ethyl group, an n-propyl group, a 2-propyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, and a 5-methylpentyl group. Examples of the cycloalkyl group include a cycloalkyl group having 3 to 16 carbon atoms, specifically including a cyclopropyl group, a cyclobutyl group, a cyclopentyl group, a cyclohexyl group, a cycloheptyl group, a 2-methylcyclopentyl group, a 3-methylcyclopentyl group, a cycloheptyl group, a 2-methylcyclohexyl group, a 3-methylcyclohexyl group, and a 4-methylcyclohexyl group. The cycloalkyl group includes a polycycloalkyl group such as a menthyl group, a bornyl group, a norbornyl group, and an adamantyl group.

Examples of the aralkyl group include an aralkyl group having 7 to 12 carbon atoms, specifically including a benzyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1-phenylpentyl group, a 2-phenylpentyl group, a 3-phenylpentyl group, 4-phenylpentyl group, a 5-phenylpentyl group, a 1-phenylhexyl group, a 2-phenylhexyl group, a 3-phenylhexyl group, a 4-phenylhexyl group, a 5-phenylhexyl group, and a 6-phenylhexyl group.

Examples of the aryl group include an aryl group having 6 to 20 carbon atoms, specifically including a phenyl group, a naphthyl group, an anthryl group, a biphenyl group, and a binaphthyl group.

Examples of the substituted hydrocarbon group include a hydrocarbon group in which at least one hydrogen atom of the above hydrocarbon group is replaced by a substituent such as a hydrocarbon group, an alkoxy group, a halogen atom, an amino group, and an amino group having a protective group; and a group in which at least one carbon atom of the above hydrocarbon group is replaced by a hetero atom such as oxygen, nitrogen, sulfur, and phosphorus.

The substituted hydrocarbon group also includes a heterocyclic group, which may be an aliphatic heterocyclic group or an aromatic heterocyclic group. Examples of the aliphatic heterocyclic group include a 5-membered or 6-membered aliphatic heterocyclic group, specifically including a pyrrolidyl-2-one group, a piperidino group, a piperazinyl group, a morpholino group, a tetrahydrofuryl group, and a tetrahydropyranyl group. Examples of the aromatic heterocyclic group include a 5-membered or 6-membered aromatic heterocyclic group, specifically including a pyridyl group, an imidazolyl group, a thiazolyl group, a furfuryl group, a pyranyl group, a furyl group, a benzofuryl group, and a thienyl group.

When it is intended to effectively induce asymmetry on the phosphorus atom in the present invention, it is preferred that $R^1$ and $R^2$ be selected so as to make a large difference in three-dimensional bulkiness therebetween. Specific examples of the preferred combination include a combination of a methyl group and a tert-butyl group and a combination of a methyl group and an adamantyl group.

When the phosphorus atom constitutes a point of the symmetry plane of axial asymmetry in the present invention, it is preferred that the moiety providing the asymmetry on $R^1$ or $R^2$ be as close as possible to the phosphorus atom so as to effectively induce asymmetry. As a specific example, there is mentioned a configuration in which $R^1$ and $R^2$ are connected to each other by crosslinking, and an atomic group including the crosslinked moiety and the phosphorus atom is 2,5-dimethylphosphorane or 2,5-diethylphosphorane.

The group represented by $R^3$ in the above general formulae (P-1), (1), and (3) is then described.

$R^3$ represents an asymmetric hydrocarbon group or an asymmetric substituted hydrocarbon group. Specific examples of the asymmetric hydrocarbon group include, but are not limited to, an (S)-1-phenylethyl group, an (R)-1-phenylethyl group, an (S)-1-(p-toluyl)ethyl group, an (R)-1-(p-toluyl)ethyl group, an (S)-1-(1-naphthyl)ethyl group, an (R)-1-(1-naphthyl)ethyl group, an (S)-1-cyclohexylethyl group, an (R)-1-cyclohexylethyl group, an (S)-2-(4-methylphenyl)-1-phenylethyl group, and an (R)-2-(4-methylphenyl)-1-phenylethyl group. Among others, the (S)-1-phenylethyl group and the (R)-1-phenylethyl group are preferred because they are industrially inexpensively available.

Examples of the asymmetric substituted hydrocarbon group include a hydrocarbon group in which at least one hydrogen atom of the above asymmetric hydrocarbon group is replaced by a substituent such as a hydrocarbon group, an alkoxy group, a halogen atom, an amino group, a nitro group, and an amino group having a protective group; and a group in which at least one carbon atom of the above asymmetric hydrocarbon group is replaced by a hetero atom such as oxygen, nitrogen, sulfur, and phosphorus.

The phosphine-borane compound of the present invention specifically includes the following compounds, but they are for illustration only, and the scope of the present invention is not limited to these compounds.

Structural formulae in the case of introducing asymmetry on the phosphorus atom are illustrated below.

[Formula 14]

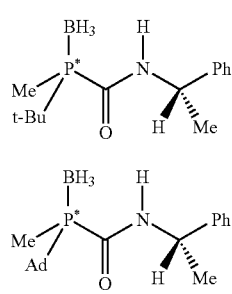

(a) (Sp)-tert-butyl(methyl)[N-((S)-1-phenylethyl)carbamoyl]phosphine-borane or (Rp)-tert-butyl(methyl)[N-((S)-1-phenylethyl)carbamoyl]phosphine-borane (b) (Sp)-adamantyl(methyl)[N-((S)-1-phenylethyl)carbamoyl]phosphine-borane or (Rp)-adamantyl(methyl)[N-((S)-1-phenylethyl)carbamoyl]phosphine-borane A structural formula in the case where the phosphorus atom constitutes a point of the symmetry plane of axial asymmetry is illustrated below.

[Formula 15]

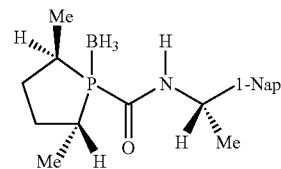

(c) (R,R)-2,5-dimethyl-1-[N-((S)-1-(1-naphthyl)ethyl)carbamoyl]phosphorane-borane The phosphine-borane compound of the present invention represented by the general formula (1) is a diastereomer having two asymmetry points characterized in that it has an asymmetric portion on the phosphorus atom or an asymmetric portion using the phosphorus atom as a point of the asymmetry plane and an optically active carbamoyl group.

A preferred embodiment of the production method of the phosphine-borane compound of the present invention will be described below.

The hydrogen-phosphine-borane compound represented by the general formula (P-2) is mixed with the optically active isocyanate compound represented by the general formula (3) in a reaction vessel, and a coupling reaction is advanced. At this time, it is preferable to add a base to the reaction system to promote the reaction. The phosphine-borane compound represented by the general formula (P-1) is produced by the coupling reaction.

The optically active phosphine-borane compound represented by the general formula (1) can be obtained by using the hydrogen-phosphine-borane compound represented by the general formula (2) as the above hydrogen-phosphine-borane compound, and after the coupling reaction, removing a by-product salt and performing purification (optical resolution) for obtaining only one of the antipodes.

The hydrogen-phosphine-borane compound represented by the general formula (P-2) or (2) may be a commercially available product, which is available, for example, from Nippon Chemical Industrial Co., Ltd. The optically active isocyanate compound represented by the general formula (3) may also be a commercially available product, which is available, for example, from Tokyo Chemical Industry Co., Ltd.

A solvent is appropriately used at the coupling reaction. A solvent which does not decompose a reactant is used as the solvent, and specific examples thereof include toluene, hexane, tetrahydrofuran (THF), diethyl ether, dioxane, acetone, ethyl acetate, chlorobenzene, dimethylformamide (DMF), acetonitrile, methanol, ethanol, and water. A preferred solvent is toluene or THF.

The addition amount of the solvent can be appropriately determined in consideration of the fluidity of the reaction mixture during the reaction and the effects the solvent exerts the reaction.

As the amount of the raw material to be charged during the reaction, the hydrogen-phosphine-borane compound represented by the general formula (P-2) or (2) is charged in amount of preferably from 0.4 to 1.5 equivalents on the basis of the optically active isocyanate compound represented by the general formula (3). The optimum value is 1 equivalent.

Addition of a base during the reaction will promote the reaction. Examples of the base used here include, but are not limited to, organic bases such as pyridine, triethylamine, tributylamine, 1,8-diazabicyclo[5.4.0]undecene-7 (DBU), 1,5-diazabicyclo[4.3.0]nonene-5 (DBN), and 4-(N,N-dimethylamino)pyridine (DMAP), inorganic bases such as sodium hydroxide, potassium hydroxide, sodium carbonate, and potassium carbonate, and organic metals such as n-butyllithium, sec-butyllithium, tert-butyllithium, lithium diisopropylamide, isopropylmagnesium chloride, and methylmagnesium bromide. Preferred is n-butyllithium.

The amount of the base to be charged can be appropriately determined depending on the degree of promotion of the reaction required. The amount is generally from 0.1 mol % to 150 mol %, preferably from 1 mol % to 10 mol %, relative to the optically active isocyanate compound represented by the general formula (3). The order of the charging is not particularly important and can be arbitrarily determined depending on workability and the like.

The reaction temperature is generally from −80 to 50° C., and is preferably from 0 to 30° C. where the reaction is promoted and a side reaction and racemization are suppressed.

The reaction time is generally from 1 minute to 24 hours, and is preferably from 30 minutes to 4 hours which is sufficient for completion of the reaction.

In producing the phosphine-borane compound represented by the general formula (1), one of the antipodes can be obtained by removing a by-product such as a by-product salt after the coupling reaction followed by optical resolution by purification. The method of purification to be performed at this time is not particularly limited as far as the optical resolution is possible, and includes separatory washing, crystallization, distillation, sublimation, and column chromatography. Crystallization is preferred because it is industrially advantageous.

The compounds represented by the general formula (1) among the phosphine-borane compounds of the present invention represented by the general formula (P-1) can be decomposed to give an optically active hydrogen-phosphine-borane compound represented by the general formula (4) which is frequently used as a raw material of the catalyst for an asymmetric synthesis reaction, with a reduced number of steps at high efficiency. Further, the compounds other than the compounds represented by the general formula (1) among the phosphine-borane compounds of the present invention, that is, those having no asymmetry on the phosphorus atom, can be used, for example, for flame retardant applications.

Hereinafter, there will be described a method for producing the optically active hydrogen-phosphine-borane compound represented by the general formula (4) using the phosphine-borane compound of the present invention represented by the general formula (1) as a raw material.

The phosphine-borane compound represented by the general formula (1) and a base are mixed in a reaction vessel to decompose the phosphine-borane compound. It is preferable to add an alcohol for promoting the decomposition reaction. A by-product is removed after the reaction to yield the optically active hydrogen-phosphine-borane compound represented by the general formula (4).

A solvent is appropriately used during the reaction. A solvent which does not decompose a reactant is used as the solvent, and specific examples thereof include toluene, hexane, tetrahydrofuran (THF), diethyl ether, dioxane, acetone, ethyl acetate, chlorobenzene, dimethylformamide (DMF), acetonitrile, methanol, ethanol, and water. A preferred solvent is DHF or acetonitrile.

The addition amount of the solvent can be appropriately determined in consideration of the fluidity of the reaction mixture during the reaction and the effects the solvent exerts the reaction.

Examples of the base include, but are not limited to, organic bases such as pyridine, triethylamine, tributylamine, 1,8-diazabicyclo[5.4.0]undecene-7 (DBU), 1,5-diazabicyclo[4.3.0]nonene-5 (DBN), and 4-(N,N-dimethylamino)pyridine (DMAP), and inorganic bases such as sodium hydroxide, potassium hydroxide, sodium carbonate, and potassium carbonate. The base is preferably supplied as a solution in order to allow it to react in a homogeneous system or in a liquid-liquid two-phase system. The solution is preferably a 1-70% solution of potassium hydroxide in water or methanol, and, for example, 50% aqueous potassium hydroxide is suitably used.

The amount of the base to be charged can be appropriately determined depending on the degree of promotion of the reaction required. The amount is generally from 0.01 equivalent to 10 equivalents, preferably from 0.1 equivalent to 5 equivalents, relative to the phosphine-borane compound represented by the general formula (1). The order of the charging is not particularly important and can be arbitrarily determined depending on workability and the like.

An alcohol is added to promote the reaction. Examples of the alcohol used here include, but not limited to, methanol and ethanol. Methanol is preferably used.

The reaction temperature is generally from −80 to 50° C., and is preferably from 0 to 30° C. where the reaction is promoted and a side reaction and racemization are suppressed.

The reaction time is generally from 1 minute to 24 hours, and is preferably from 3 hours to 20 hours which is sufficient for completion of the reaction.

The resulting product after the reaction can be used either after a simple purification operation such as only removing a by-product salt or after isolating the optically active hydrogen-phosphine-borane compound represented by the general formula (4) by a purification operation such as separatory washing, crystallization, distillation, sublimation, and column chromatography.

The phosphine-borane compound of the present invention is useful for the production of an optically active phosphine ligand frequently used as a raw material of the catalyst for an asymmetric synthesis reaction because it easily decomposes as described above to produce an optically active hydrogen-phosphine-borane compound. Further, the method for producing the phosphine-borane compound of the present invention is industrially useful because it can produce the above described phosphine-borane compound with a reduced number of steps at high efficiency. Furthermore, the method for producing the optically active hydrogen-phosphine-borane compound of the present invention is useful for the production of an optically active phosphine ligand frequently used as a raw material of the catalyst for an asymmetric synthesis reaction. From these facts, the present invention can greatly contribute to the production of the optically active phosphine ligand frequently used as a raw material of the catalyst for an asymmetric synthesis reaction.

EXAMPLES

The present invention will now be specifically described with reference to Examples, but they are for illustration only, and the scope of the present invention is not limited thereto.

All the synthetic operations were performed using thoroughly dried glassware. The reaction was performed in a nitrogen atmosphere. The raw materials and solvent used were general reagents. The racemic tert-butylmethylphosphine-borane used was manufactured by Nippon Chemical Industrial Co., Ltd.

NMR spectrum measurement was performed using an NMR spectrometer from JEOL, Ltd. ($^1$H: 300 MHz, $^{13}$C: 75.4 MHz, $^{31}$P: 121.4 MHz). Tetramethylsilane ($^1$H) was used as an internal standard. Specific rotation measurement was performed using a polarimeter SEPA-300 manufactured by Horiba, Ltd.

Example 1

Production of (Sp)-tert-butyl(methyl)[N-((S)-1-phenylethyl)carbamoyl]phosphine-borane A 3-liter 4-mouth flask was equipped with a mechanical stirring seal, a thermometer, a pressure-equalizing dropping funnel, and an exhaust part. The flask was charged with 141.8 g (1202 mmol) of racemic tert-butylmethylphosphine-borane and 600 cc of THF to dissolve the racemic tert-butylmethylphosphine-borane. To the resulting solution were dropped 75 cc (119 mmol) of a 1.59 mol/L n-butyllithium/hexane solution while keeping the solution at 10° C. or less. Subsequently, thereto were dropped 176.8 g (1201 mmol) of (S)-(−)-α-methylbenzyl isocyanates at the same temperature. The resulting mixture was then returned to room temperature and aged overnight with stirring. The reaction was stopped by adding 90 g of 5% by weight hydrochloric acid, and then the mixture was separated into two layers by adding 240 cc of hexane and 240 cc of water. The water layer was removed, and the organic layer was washed successively with 240 g of 2.5% by weight sodium bicarbonate water and 240 cc of water and concentrated to yield a coarse product as a white flaky solid (348.3 g). The coarse product was crystallized with 240 cc of ethyl acetate and 1800 cc of hexane, filtered, and dried to yield a colorless powder. The resulting colorless powder was identified as the title compound by NMR analysis. NMR analysis results are shown below. The resulting colorless powder had a yield of 118.6 g (447 mmol), a percent yield of 37% (based on isocyanate), and a diastereomer excess of >97%. Note that the diastereomer excess was determined from the area ratio of the protons in specific portions of SP and RP of $^1$H-NMR.
(NMR Analysis Results)
[$^1$H-NMR (CDCl$_3$)]
(Sp)-form (target substance); −0.5-1 (3H, m), 1.14 (9H, d, 14.7 Hz), 1.45 (3H, d, 10.5 Hz), 1.53 (3H, d, 6.9 Hz), 5.15 (1H, pent, 6.9 Hz), 7.2-7.4 (6H, m).
(Rp)-form; −0.5-1 (3H, m), 1.25 (9H, d, 14.7 Hz), 1.42 (3H, d, 10.5 Hz), 1.53 (3H, d, 6.9 Hz), 5.15 (1H, pent, 6.9 Hz), 7.2-7.4 (6H, m).

Example 2

Production of an Optically Active Hydrogen-Phosphine-Borane Compound [(R)-tert-butylmethylphosphine-borane]

A 200-cc 4-mouth flask was equipped with a mechanical stirring seal, a thermometer, and an exhaust part. The flask was charged with 10.03 g (37.8 mmol) of (Sp)-tert-butyl (methyl)[N-((S)-1-phenylethyl)carbamoyl]phosphine-borane obtained in Example 1 and 100 cc of DMF to dissolve the phosphine-borane. The resulting solution was cooled to 10° C. or less in an ice-water bath. Thereto were added 21.26 g (189 mmol) of 50% by weight aqueous potassium hydroxide and 25 cc of methanol. The ice-water bath was then removed, and the mixture was aged for 18 hours with stirring. Subsequently, a 500-cc Erlenmeyer flask was charged with 100 cc of cold water and 100 cc of petroleum ether, and the reaction mixture was dispersed therein to stop the reaction. The water layer and the organic layer were separated, and the water layer was re-extracted with 100 cc of petroleum ether. The resulting petroleum ether was combined with the organic layer separated earlier. The resulting organic layer was washed twice with 50 cc of water and dried over anhydrous sodium sulfate. The resulting organic layer was purified by silica gel column chromatography (Wako gel C-200) to yield a colorless powder. The resulting colorless powder was identified as the title compound by NMR analysis. NMR analysis results are shown below. The resulting colorless powder had a yield of 3.01 g (25.5 mmol) and a percent yield of 67%.
(NMR Analysis Results)
$^1$H-NMR (CDCl$_3$);
−0.5-1 (3H, m), 1.22 (9H, d, 14.7 Hz), 1.32 (3H, d, 10.5 Hz, 6.0 Hz), 4.4 (1H, dm, 355 Hz).

Example 3

Production of an Optically Active Hydrogen-Phosphine-Borane Compound [(R)-tert-butylmethylphosphine-borane]

A 300-cc 4-mouth flask was equipped with a mechanical stirring seal, a thermometer, and an exhaust part. The flask was charged with 7.97 g (30.1 mmol) of (Sp)-tert-butyl(methyl)[N-((S)-1-phenylethyl)carbamoyl]phosphine-borane obtained in Example 1 and 30 cc of DMF to dissolve the phosphine-borane. The resulting solution was cooled to 10° C. or less in an ice-water bath. Thereto were added 3.37 g (6.0 mmol, 20 mol %) of 10% by weight potassium hydroxide/methanol solution. The ice-water bath was then removed, and the mixture was aged at room temperature for 18 hours with stirring. Subsequently, the flask was charged with 3.07 g (4.2 mmol) of 5% hydrochloric acid to stop the reaction and then charged with 30 cc of hexane and 60 cc of water to separate the reaction mixture into two layers. The water layer and the organic layer were separated, and the water layer was re-extracted 3 times with 10 cc of hexane. The resulting hexane was combined with the organic layer separated earlier. The resulting organic layer was washed with 30 cc of water and 30 g of 20% saline solution and dried over anhydrous sodium sulfate. The resulting organic layer was purified by silica gel column chromatography (Wako gel C-200) to yield a colorless powder. The resulting colorless powder had a yield of 2.57 g (21.8 mmol) and a percent yield of 72.5%. The resulting colorless powder was identified as the title compound since NMR analysis showed a chart shape equivalent to the compound obtained in Example 2.

Use Example 1

There is shown below a use example in which (R)-tert-butylmethylphosphine-borane obtained in Example 2 is used to synthesize (S,S)-2,3-bis(tert-butylmethylphosphino)quinoxaline [abbreviation: (S,S)-QuinoxP*] known as an asymmetric phosphine ligand.

The title compound was obtained as an orange powder by synthesizing it in substantially the same procedure as described in the literature of J.A.C.S, 127 (2005), 11934 to 11935 using 3.01 g (25.5 mmol) of (R)-tert-butylmethylphosphine-borane obtained in Example 2 and 1703 mg (8.56 mmol) of 2,3-dichloro quinoxaline. The yield was 2149 mg (6.427 mmol) and the percent yield was 75%. The analysis results of the resulting orange powder are shown below.
(Analysis Results)
$^1$H-NMR (CDCl$_3$): Equivalent to that given in the above literature.
Specific rotation: +53.5° ([α]$_D^{22}$ (c=1, CHCl$_3$), the literature value: −54.3° as (R,R)-QuinoxP)

Use Example 2

There is shown below a use example in which (R)-tert-butylmethylphosphine-borane obtained in Example 2 is used to synthesize (R,R)-1,2-bis(tert-butylmethylphosphino)ethane-diborane [abbreviation: (R,R)-BisP*-diborane] known as a precursor of an asymmetric phosphine ligand.

A 300 4-mouth flask was equipped with a mechanical stirring seal, a thermometer, a pressure-equalizing dropping funnel, and an exhaust part. The flask was charged with 5.28 g (448 mmol) of (R)-tert-butylmethylphosphine-borane and 50 cc of THF to dissolve the (R)-tert-butylmethylphosphine-borane. To the resulting solution were dropped 25 cc (42.9 mmol) of 1.59 mol/L n-butyllithium/hexane solution while keeping the solution at 0° C. or less. Thereto were added 1.38 g (14.0 mmol) of 1,2-dichloroethane at the same temperature. The resulting mixture was then returned to room temperature and aged for 4 hours with stirring. The reaction was stopped by adding 30 cc of water and 10 g of 5% by weight hydrochloric acid, and then the mixture was separated into two layers by adding 60 cc of ethyl acetate. The water layer was removed, and the organic layer was washed successively with 30 g of 2.5% by weight sodium bicarbonate water and 30 cc of water and concentrated to yield a coarse product as a white flaky solid (4.92 g). The coarse product was crystallized with 70 cc of methanol, filtered, and dried to yield the title compound as a colorless powder. The yield was 3.18 g (12.1 mmol) and the percent yield was 86.8% (from dichloroethane). The analysis results of the resulting colorless powder are shown below.

(Analysis Results)

$^1$H-NMR (CDCl$_3$): Equivalent to that described in J.A.C.S., 120 (1998), 1635 to 1636.

Specific rotation: +9° ([α]$D_{27}$ (c=1, CHCl$_3$), the literature value: −9.1° as (S,S)-BisP*-diborane)

What is claimed is:

1. A phosphine-borane compound represented by general formula (P-1):

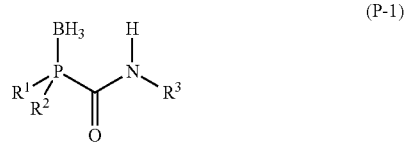

(P-1)

wherein $R^1$ and $R^2$ each independently represent a hydrogen atom, a hydrocarbon group, or a substituted hydrocarbon group; and $R^3$ represents an asymmetric hydrocarbon group or an asymmetric substituted hydrocarbon group.

2. The phosphine-borane compound according to claim 1, wherein the phosphine-borane compound is represented by general formula (1):

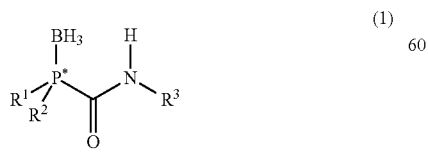

(1)

wherein $R^1$ and $R^2$ are a pair of groups which induce asymmetry on the phosphorus atom by the presence of these groups or form an asymmetry plane using the phosphorus atom as a point of the plane, wherein the $R^1$ and $R^2$ each represent a hydrogen atom, a hydrocarbon group, or a substituted hydrocarbon group; $R^3$ represents an asymmetric hydrocarbon group or an asymmetric substituted hydrocarbon group; and the asterisk * represents asymmetry.

3. The phosphine-borane compound according to claim 1 or 2, wherein the $R^3$ is an (S)-1-phenylethyl group or an (R)-1-phenylethyl group.

4. A method for producing a phosphine-borane compound according to claim 1, the method comprising subjecting a hydrogen-phosphine-borane compound represented by general formula (P-2):

(P-2)

(wherein $R^1$ and $R^2$ have the same meaning as in the above general formula (P-1)) to a coupling reaction with an optically active isocyanate compound represented by general formula (3):

[Formula 4]

(3)

wherein $R^3$ has the same meaning as in the above general formula (P-1).

5. A method for producing a phosphine-borane compound according to claim 2, the method comprising the steps of subjecting a hydrogen-phosphine-borane compound represented by general formula (2):

(2)

(wherein $R^1$ and $R^2$ have the same meaning as in the above general formula (1)) to a coupling reaction with an optically active isocyanate compound represented by general formula (3):

(3)

wherein $R^3$ has the same meaning as in the above general formula (1); and then purifying the resulting compound by optical resolution.

6. A method for producing an optically active hydrogen-phosphine-borane compound represented by general formula (4):

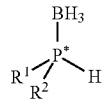
(4)

wherein $R^1$, $R^2$, and the asterisk * have the same meanings as in the above general formula (1), the method comprising subjecting a compound according to claim 2 to a decomposition reaction.

7. A phosphine-borane compound according to claim 2 used for producing an optically active hydrogen-phosphine-borane compound represented by general formula (4):

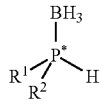
(4)

wherein $R^1$, $R^2$, and the asterisk * have the same meanings as in the above general formula (1).

* * * * *